(12) United States Patent
Thompson et al.

(10) Patent No.: US 9,733,224 B2
(45) Date of Patent: *Aug. 15, 2017

(54) SOLAR POWERED SAMPLE ANALYZING SYSTEM USING A FIELD DEPLOYED ANALYTICAL INSTRUMENTATION AND VACUUM JACKETED SMALL DIAMETER TUBING

(71) Applicant: Mustang Sampling, LLC, Ravenswood, WV (US)

(72) Inventors: Kenneth O. Thompson, Ravenswood, WV (US); Claude A. Rolston, St.Marys, WV (US); Timothy L. Querrey, Murraysville, WV (US); Charles F. Cook, Humble, TX (US)

(73) Assignee: Mustang Sampling LLC, Ravenswood, WV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/255,371

(22) Filed: Sep. 2, 2016

(65) Prior Publication Data
US 2016/0370328 A1  Dec. 22, 2016

Related U.S. Application Data

(63) Continuation of application No. 14/515,603, filed on Oct. 16, 2014, now Pat. No. 9,459,185.
(Continued)

(51) Int. Cl.
| | | |
|---|---|---|
| *G01N 33/00* | (2006.01) | |
| *G01N 1/22* | (2006.01) | |
| *G01N 30/88* | (2006.01) | |

(52) U.S. Cl.
CPC .......... *G01N 30/88* (2013.01); *G01N 1/2247* (2013.01); *G01N 33/0016* (2013.01); *G01N 33/0075* (2013.01); *G01N 2030/8881* (2013.01)

(58) Field of Classification Search
CPC ...... G01N 1/2247; G01N 1/10; G01N 1/2035; G01N 1/22; G01N 2001/2285; G01N 33/0009
See application file for complete search history.

(56) References Cited

U.S. PATENT DOCUMENTS

| | | |
|---|---|---|
| 5,501,080 A | 3/1996 | McManus et al. |
| 6,386,014 B1 | 5/2002 | Butch |

(Continued)

FOREIGN PATENT DOCUMENTS

KR   101286951 B2   12/2011

OTHER PUBLICATIONS

International Application No. PCT/US2014/060829 Notification of Transmittal of the International Search Report and the Written Opinion of the International Searching Authority, or the Declaration, dated Feb. 2, 2015.

*Primary Examiner* — David A Rogers
(74) *Attorney, Agent, or Firm* — Cahn & Samuels, LLP

(57) ABSTRACT

Provided herein is a solar powered system for a gas sampling and analysis for placement and operation remote from conventional infra-structure that utilizes a minimum of power to obtain a sample extracted from a source such as a pipeline or well-head, conditions the extracted sample, transmits the conditioned sample through vacuum jacketed tubing to an analyzer while maintaining the sample at a temperature and pressure preventing phase transition, condensation or component partitioning.

16 Claims, 4 Drawing Sheets

Related U.S. Application Data

(60) Provisional application No. 61/892,029, filed on Oct. 17, 2013.

(56) References Cited

U.S. PATENT DOCUMENTS

| | | | |
|---|---|---|---|
| 7,162,933 B2 * | 1/2007 | Thompson | G01N 1/2214 73/863.11 |
| 7,484,404 B2 | 2/2009 | Thompson et al. | |
| 7,743,641 B2 | 6/2010 | Bailey et al. | |
| 7,763,474 B2 | 7/2010 | Hassell | |
| 7,795,837 B1 | 9/2010 | Haun et al. | |
| 8,056,399 B2 | 11/2011 | Thompson et al. | |
| 9,164,016 B2 * | 10/2015 | Barere | F17C 7/04 |
| 2002/0023479 A1 | 2/2002 | Burge et al. | |
| 2004/0200537 A1 | 10/2004 | Rivest | |
| 2005/0095380 A1 | 5/2005 | Watkins et al. | |
| 2006/0000298 A1 | 1/2006 | Thompson et al. | |
| 2006/0093523 A1 | 5/2006 | Norman | |
| 2006/0202122 A1 | 9/2006 | Gunn et al. | |
| 2009/0071235 A1 | 3/2009 | Gross | |
| 2010/0137729 A1 | 6/2010 | Pierry et al. | |
| 2010/0260551 A1 | 10/2010 | Jespersen | |
| 2010/0283991 A1 | 11/2010 | Chrzan et al. | |
| 2012/0017669 A1 * | 1/2012 | Thompson | F17C 6/00 73/61.59 |
| 2012/0109583 A1 | 5/2012 | Bartlett et al. | |
| 2012/0198912 A1 | 8/2012 | Ewing et al. | |
| 2012/0325694 A1 | 12/2012 | Thompson | |
| 2014/0144254 A1 * | 5/2014 | Thompson | G01N 1/2247 73/863.11 |

\* cited by examiner with # SOLAR POWERED SAMPLE ANALYZING SYSTEM USING A FIELD DEPLOYED ANALYTICAL INSTRUMENTATION AND VACUUM JACKETED SMALL DIAMETER TUBING

PRIORITY CLAIM

This application is a continuation of application Ser. No. 14/516,603 filed on Oct. 16, 2014, now U.S. Patent and claims priority to U.S. Patent Application Ser. No. 61/892,029 filed Oct. 17, 2013.

FIELD OF INVENTION

This invention relates to a self-contained, integrated analyzing system with minimized power usage requirements including an operating power source for sample takeoff and analysis particularly suited for a wet gas from a pipeline at custody transfer points, intermediate gather points, remote field gather points, and the like. The invention combines an integrated low-power source for processing operations, low-power heaters and pressure regulators, small-diameter vacuum jacketed tubing (VJT) for vaporized sample gas transport between a conditioning unit and an associated analyzer to prevent flashing of heavy sample constituents, and low-power processing control and remote communication components. The invention is readily adaptable to conform to specific safety and regulatory requirements, for example, by enclosure in one or more explosion proof housings to meet area classifications.

BACKGROUND

Liquid sample extraction and vaporization analysis in chemical and petrochemical processing is well-known and well-established. Vaporized samples extracted from a source are used for processing control, pollution monitoring, purity analysis, energy content auditing, etc. In such cases, it is important that the constituents of the vaporized sample correspond to the composition of the extracted sample. In the case of a natural gas pipeline for energy audit purposes, it is desirable to conduct sample analysis extraction at custody transfer points along the gas distribution pathway, e.g., at the wellhead, at compression into liquid, at injection into a main pipeline, at regasification, etc.

It is well documented that the natural gas industry has experienced rapid growth and generated a significant need for field deployable analyzing capabilities. For example, in the United States alone, shale oil & gas extraction activities in the Marcellus Formation, Eagle Ford, and Bakken deposits have generated numerous new drilling fields, pipeline injection and gathering points and custody transfer points that are remotely-sited from conventional infrastructure, e.g. sources of electric power and telemetric communication. Consequently, sample take-off and analyzing operations at such points are curtailed if not altogether prevented unless a temporary source of electrical power and communication is provided.

To this end, the natural gas industry has turned in some instances to conventional gas or diesel powered electric generators for powering sample takeoff and analyzing equipment. However, reliance on such generators, itself, creates logistical and maintenance issues. First, there is the need for regular resupply of the generator fuel in addition to the requirement for engine maintenance both of which require vehicular road access to the site of the analyzing equipment.

One known solution to overcome to reliance on such power generation methods where the pipeline product involved is natural gas involves tapping directly into the pipeline and extracting natural gas for a natural gas (NG) powered generator. One significant drawback from such an arrangement is the need for construction of an independent pipeline takeoff connection to the generator. In an NG environment, specially trained technicians are required for such installations. Subsequently, if a conventional power source such as an overland power line becomes available, the takeoff connection must either be deactivated or removed.

Consequently, when a new extraction field is developed remote from power and telephone lines, either at least one new line must be strung with its concomitant adverse environmental impact or multiple generator units need to be transported, positioned, maintained and fueled to power a discrete array of analyzer units various flow control and conditioning equipment, analyzers, communication and computer control units associated with the extraction. At a cost, presently at about \$75,000 (€ 50,000) for each installation, reliance on such electrical generator units can result in substantial unrecoverable costs.

A further consideration results from the extraction of a "Wet" gas from wells. Although natural gases obtained from wells are predominantly methane, certain shale—derived gases comprise a significant amount of C2 to C5 hydrocarbons and up to C8 hydrocarbon constituents—"heavies". "Dry" gas, containing minimal "heavies" is not significantly affected by differential temperature and pressure within the pipeline and/or at the regulator inlet and outlet. However, "Wet" gas characteristically includes a significant proportion of "heavies" which leads to dew point dropout/phase transition in cases of fluctuating temperature and pressure. For example, liquid pressure diminishes upon removal from the pipeline stream at take-off and during transit to an analyzer unit. Such fluctuations induce partitioning of the heavies whether in a liquid or vapor phase. It is therefore important to maintain consistent sample temperature and pressures regardless of the sample phase during the entire duration of transit from take-off to vaporizer and from vaporizer to analyzer.

Liquid intrusion into an analyzing system is unacceptable to the extent that the present ISO 8943 standard requires restriction of liquid flow to the conditioning vaporizer in order to prevent flooding of the system. The conventional approach to satisfy this requirement is to incorporate a flow restrictor. However, if the sample is a "Wet" NG, an in-line flow restrictor will induce in-line pressure changes causing partitioning/flashing of the heavies into discernable fractions. That is, the lights partition from the heavy components where the lighter constituents pass first into the vaporizer before the heavies. The presence of the differently-constituted fractions skews the accuracy of the content analysis which implicates the accuracy of the energy content measurements. Where such partitioning is combined because of inconsistent temperature and pressure, a phase transition curve may be violated inducing Joules-Thompson condensation of the partitioned vapor into a liquid phase. In the case of a system using a gas chromatograph (GC) for analysis, injection of a liquid into a GC will damage the analyzer.

Therefore, a need exists for an integrated sample take-off, analytical system that is self-powering, easily transportable, capable of two-way telemetry, and provides low-power sample take-off conditioning to an associated low-power analyzer that minimizes risk of vapor sample phase partition and condensation or transition. The system preferably also meets regulatory and safety requirements while being field deployable, particularly in the case of newly-established "wet" natural gas extraction resources and transfer points remotely located from conventional infrastructure.

SUMMARY OF THE INVENTION

It is an object of the present invention to overcome shortcomings of existing art.

It is an object of the present invention to provide a solution to operation of instrumentation required for fluid sample takeoff, conditioning, and accurate content analysis remote from existing power and communications infrastructure.

It is another object of the present invention to provide an energy self-sufficient, wet or dry gas sample conditioning system that provides accurate content analysis.

These and other objects are satisfied by a system for extracting and analyzing a sample from a pipeline, the system comprising: a pipeline sample take-off probe; a take-off conduit connecting said takeoff probe to a sample conditioner to generate a vaporized sample, said sample conditioner including an electrically powered heater element, a pressure regulator, flow controller, and a conditioned vaporized sample output; a vacuum jacketed insulated tubing defined by an outer tubular casing with an inner surface and an inner tubular vaporized sample conduit member an inner and outer surface, said inner tubular vaporized sample conduit member with a first and a second end where the first end is attached to said conditioned vaporized sample output of said sample conditioner, said inner tubular vaporized sample conduit member being substantially coextensive with and coaxially disposed within said outer tubular casing and spaced therefrom so as maintain space between it and said inner surface of said outer tubular casing to form a thermal insulating annulus between said outer casing inner surface and said inner tubular vaporized sample conduit member outer surface, and said inner tubular vaporized sample conduit member defining a wall having a thickness sufficient to possess a pressure rating in excess of 500 psig, an preferably exceeding 4000 psig (35-270 bar) and to allow for non-destructive bending, and said inner tubular vaporized sample conduit member having an inner diameter dimensioned to maintain sufficient pressure and flow rate to avoid flashing during transit threrethrough, and an electrically powered analyzer unit including a low power vapor analyzer for qualitative and quantitative detection of at least one analyte in said conditioned vaporized sample, said analyzer unit having an inlet in vapor communication with said second end of the tubular vaporized sample conduit member for receiving said conditioned vaporized sample, an input for a carrier gas, said electrically powered analyzer detecting the at least one analyte of the vaporized sample and generating at least one signal corresponding to the obtained result; an electrically powered wireless communications module unit for transmitting the results to a remote receiver; a low power electrical control unit including a power control center electrically connected to each of the conditioner, analyzer unit and wireless communication module; and a photovoltaic panel with an electrical power storage array connected to the low power control unit for distribution to electrically-operated control unit.

The foregoing and still other objects are satisfied by a solar-powered system for analyzing fluid samples, the system comprising: a first enclosure including a heated fluid sample take-off input, a heated pressure regulator, a flow conditioner, and a conditioned vaporized sample output, wherein the first enclosure is in operable communication with a sample source and generates a conditioned vaporized gas sample from the fluid; a second enclosure operably connected to the first enclosure, said second enclosure including a conditioned sample input and an analyzing device providing a signal output representative of the vaporized gas sample composition; means for communicating said conditioned vaporized gas sample between said first and second enclosure in a manner to maintain thermal and flow rate stasis of the vaporized sample during transit, and a third enclosure including a power control center, a photovoltaic panel, and a communication containing module for providing operating power to the first and second enclosures and receiving said signal from the analyzing device.

In short, the invention contemplates an array of components for sample analysis that in one embodiment provides an integrated, sample take-off analysis station that employs a remotely-spaced, field gas chromatograph where a conditioned gas take-off sample is transferred thereto via vacuum jacketed tubing (VJT) that maintains the sample temperature and pressure during transit and a digital signal transceiver for wirelessly communicating obtained analytical data from the chromatograph to a remote base collection station where all energy consuming components are electrically powered by a self-sustaining, stand-alone energy source such as a solar-powered array with battery storage.

The invention contemplates a combination of elements for a gas sampling and analysis system that utilizes a minimum of power to obtain a sample, particularly of a heavies-containing wet gas, extracted from a source such as a pipeline or well-head, condition the extracted sample, to transmit the conditioned sample while maintaining the sample at a temperature and pressure preventing partitioning and/or phase transition/Joule-Thompson type condensation/dew-point dropout, to analyze the extracted sample, and to communicate the obtained results to a remote information receiving and control station where the system is powered by solar energy.

The invention operates at low power, e.g., 12 or 24 volts, and is readily transportable, deployable and operable in locations remote from existing infrastructure while meeting applicable safety and regulatory requirements including, if necessary, explosion-proof containment. Not only does the incorporation of reduced size low power components such as 12 or 24 Volt DC heaters and pressure regulators in the invention reduce the operational energy requirements and size of any containment housings but it also provides the collateral benefit of reducing the requirements for termination and end seal electrical kits to meet Class 1-Division 1, explosion proof thresholds.

Critical to the invention is its capability to assure accurate measurements by maintaining the vaporized sample at a temperature and pressure from take-off to analysis in a manner avoiding phase transfer or flashing/partitioning of vaporized constituents. The low power, integrated, analyzer system of the invention is readily adapted for placement in newly-established natural gas gathering systems, remote pipeline transmission points, and/or largely inaccessible locations to provide periodically scheduled, on-demand, and even optionally, composite pipeline sample analysis such as that described in commonly-owned application U.S. Ser. No. 14/205,526 filed Mar. 12, 2014 and incorporated herein by reference.

The system of the present invention essentially comprises three discrete components. The first is a heated sample take-off unit. A preferred sample takeoff array is of the type sold by Mustang Sampling LLC, under the name PONY® and described in U.S. Pat. No. 7,162,933 incorporated herein by reference. The present invention modifies the heated sample take-off unit to include a sample takeoff probe, a low-power heater, a low power pressure regulator with a conditioned gas output and electrically operable control-valve flow control.

The second component of the invention which for nomenclature purposes here, is referred to as the analyzer array, includes a conditioned gas input from the heated sample conditioning unit, an electrically operated solenoid vacuum valve port with a vacuum status indicator, a low power flow conditioning control panel, a lower power field-type process gas analyzer, for example, a gas chromatograph such as a Model PGC1000 from ABB Ltd. of Switzerland, a solenoid valve operated carrier gas input port, e.g., helium, a power cable input, power output connection, and a small diameter vacuum jacketed tubing connection extending between the first and second components for non-phase transfer of the heated and conditioned sample gas there between without need for an auxiliary heat source such as heat trace cable and the like to maintain temperature during transfer.

The third component is referred to as the power center component. It includes a solar power collecting photovoltaic cell array and deep-cycling battery-type energy storage cells connected to a system power control center and communication/telemetry facility to provide the requirements to each of the electrically operable components via independent heat trace cabling or via wiring sealed within and extending through an approved form of conduit and sealing system that meet applicable requirements for hazardous area classification by the National Electric Code (NEC). Notably, in a preferred mode, the reliance on the VJT dispenses with the need for heat trace cabling to maintain temperatures in the vacuum jacketed tubing. Although heat tracing is employable in the context of the current invention, its power requirement corresponding to approximately 5 W per linear foot (30 cm) is eliminated when the heat trace is substituted for by VJT.

The present invention, in a preferred mode, uses vacuum jacketed small diameter tubing to dispense with the need for operationally disposed heat tracing over the length of the connection between the sample take-off and conditioner to the analyzer. The vacuum jacketed tubing in this case relies on a small diameter stainless steel tube of up to 30 feet (10 meters) in length. The tube, preferably composed of 316 stainless steel possessing a relatively heavy wall (0.065 in.) for strength, has an outer diameter ranging from $\frac{1}{16}$ inch (0.16 cm) to as much as $\frac{3}{8}$ inch (0.9 cm) for communicating a vaporized sample and an inner diameter adapted to ensure transit time for a fresh sample to be introduced to the analyzer for each analyzing cycle. The use of the small diameter VJT decreases lag time between conditioning and analysis, maintains the vapor at a consistent temperature during transit with minimal heat loss, and prevents the vapor from condensing by maintaining the pressure at a threshold well above the phase transition curve. This temperature maintenance objective is achieved whether the vapor is a hot gas or at cryogenic temperatures.

The use of a small bore take-off probe connected with by small bore, heavy walled-tubing for communicating the sample to the vaporizer avoids composition/energy content analysis error by minimizing the creation of intra-tube turbulence of the kind typically resulting from the use of a restrictor as well as avoiding generation of venturi effects on the liquid passing through a restrictor. Furthermore, measurement reliability and accuracy is improved due to the reduced resident lag time of the vaporized sample in the tube minimizing the concomitant partitioning/separation of heavier and lighter components of the sample during transit.

In one embodiment of the invention, the first three components are separated and spaced apart, the heated sample take-off unit and the analyzer array units also being contained in explosion-proof housing enclosures. The invention also contemplates convertibility. For example, in one embodiment, the power center establishes a discretely housed module from the take-off unit and analyzer housing enclosure(s). When conventional infrastructure, e.g., new power lines or the like are brought into the vicinity of the system, the power center may be disconnected in favor of the power line source and moved to a new site to be "plugged" into another remote the take-off/sample analyzer at another transfer point. To take advantage of the full convertibility, the components may also be mounted on a skid or trailer(s) for rapid movement by helicopter or truck to a select transfer takeoff point or the like. In this fashion, the invention is readily usable in connection with recently established fields where the typical infrastructure has not yet been established.

In this detailed description, references to "one embodiment", "an embodiment", or "in embodiments" mean that the feature being referred to is included in at least one embodiment of the invention. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the root terms "include" and/or "have", when used in this specification, specify the presence of stated features, steps, operations, elements, and/or components, but do not preclude the presence or addition of at least one other feature, step, operation, element, component, and/or groups thereof.

As used herein, "analyte" contemplates a constituent from a source such as natural gas, a liquid natural gas, natural gas liquid, or a cryogenic liquid capable of vaporization and sample content characterization by conventional analysis equipment such as a gas chromatograph, mass spectrograph, Raman spectrophotometer, tunable diode laser spectrograph, etc.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

For definitional purposes and as used herein "connected" includes physical, whether direct or indirect, affixed or adjustably mounted, as for example, the communication unit is connected to the a sample analyzer component either directly or through a conventional wireless linkage when spaced apart. Thus, unless specified, "connected" is intended to embrace any operationally functional connection.

As used herein, "process gathering point" and "transfer point processing" means the location for and processes involving the transfer and movement of a fluid analyte from one place to another in the conventional sense, such as via a pipeline network from removal to transmission/transport/storage e.g., a well in a drilling field through intermediate connection points and processing lines to gathering points or storage and insertion into main gas transmission lines as well to or from any transport vehicles such as ships, barges, and railcars.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawings which are provided for illustration purposes as representative of a specific exemplary embodiment in which the invention may be practiced. The following illustrated embodiment is described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION OF THE ILLUSTRATED EMBODIMENT OF THE INVENTION

Figure 1:
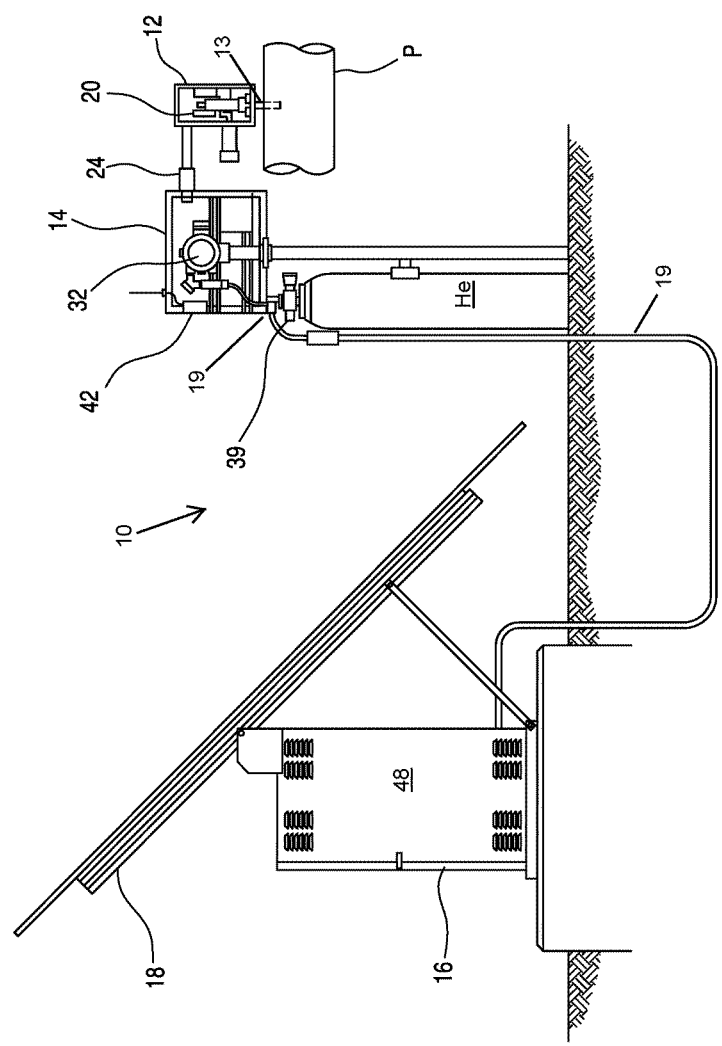
FIG. 1 is a schematic of an embodiment of a low power solar powered sample conditioning and analyzing system according to the invention.

FIG. 1 schematically illustrates analyzer system 10 according to an embodiment of the present invention. The analyzer system 10 essentially comprises three discrete components which in the illustrated embodiment are contained in separate, spaced-apart cabinet enclosures. The components are probe take-off unit 12 which is attached to transmission pipeline P, analyzer unit 14, and solar power generation and storage module 16 to which photovoltaic panel 18 is adjustably and electrically mounted.

The probe take-off unit 12 incorporates a take-off probe 13 connected to an electrically powered, heated pressure regulator 20 and flow conditioner for conditioning samples withdrawn from the pipeline P which contain at least one constituent qualifying as an analyte. The sample take-off unit 12, itself, is heated to avoid sample dew-point drop-out. Such a unit is available from Mustang Sampling LLC, under the name PONY® and described in U.S. Pat. No. 7,162,933 incorporated herein by reference. In brief, the Pony cabinet includes a heater, a gas pipeline takeoff probe, a heated regulator, flow conditioner, and conditioned gas output. The power for the components is provided by a heat tracing electrical conduit 22 from the below-described analyzer cabinet 14.

The second enclosure cabinet 14 which for nomenclature purposes here, is called the analyzer cabinet, includes selectively latchable, hingedly connected, sealable front door 15, exterior latches 17, a conditioned gas input 22, a vacuum valve port 26 with a vacuum status indicator 28, a flow conditioning control panel 30, an electrically powered, field-type process gas chromatograph 32 such as a Model PGC1000 from ABB Ltd. of Switzerland, a carrier gas, e.g., helium input port 34, a power input 19, power output junction 36, and vacuum jacketed tubing 24 for thermally static transference of heated and conditioned gas sample between the first enclosure 12 and the second enclosure 14. As is the case of an analyzer, it requires a particular dwell time (time of residence in the analyzer) of the sample to obtain proper measurements. The sample dwell time results in a periodic sample cycle that requires a fresh sample input for each cycle. It also should be noted that any or all of the enclosures may be constructed to be explosion proof to meet National Electrical Code Class 1, Division 1, Groups C and D with a T3 maximum temperature rating for North America or ATEX and IEC Zone 1 standards.

The vacuum jacketed tubing 24 (VJT) connecting the sample conditioning cabinet and the analyzer cabinet preferably is constructed using a relatively long length of, e.g., twelve feet (3.5 m), of ¼ inch outer diameter 316 stainless steel vapor sample conduit tubing member 51. (The tube member length may extend up to 10 meters). The length of the tubing member is restricted to a maximum distance corresponding to the distance where the vacuum tubing effectively maintains thermal stasis and preserves the heated gas sample at a pressure preventing partitioning and/or dew point dropout during transit between the takeoff unit 12 and cabinet 14, without the need for an auxiliary heat source, e.g., heat trace cable. The use of vacuum jacketed tubing to maintain sample temperatures above the condensation point is an important aspect of the invention because it eliminates the need to heat the transport tubing and for electrical power to operate an independent heat source. The use of vacuum jacketed tubing 24 also dispenses with the need for including an auxiliary heater in the analyzer cabinet as a result of preserving of the heat content of the gas sample passed to the analyzer.

The vaporized sample conduit member 51 preferably has a ⅛ to ¼ outer diameter with a wall thickness of from 0.025 to 0.065 inch which provides a burst pressure rating of in excess of 4000 psig (~270 bar) and up to 12,000 psig (~800 bar). The conduit member is bendable without creasing/pinching at least during its installation and the inner diameter of the member 51 is selected to maintain sufficient pressure at a flow rate that avoids flashing from phase transition and partitioning during transit from said first end to a second end. In application, the tube dimensional parameters are selected to provide a end-to-end transit time of the sample corresponding to the measuring cycle of and provide a fresh sample to the attached analyzer, where the analysis is not continuous as in the case of a tunable laser diode unit. Accordingly, the tube measurement can range in imperial units from 1/16 to 3/8 inch outer diameter with wall thickness of 0.020 to 0.065 inch (3 mm-8 mm) outer diameter with a 0.5 to 1.5 mm wall thickness, in metric units) to provide pressure ratings up to about 10,200 psig (~700 bar).

Except for the terminal ends of the tubing member 51, it is substantially covered by a coaxially disposed 1½-2 inch (2-5 cm) outer diameter stainless steel vacuum jacket 52, each end of which is hermetically secured by a stainless steel compression fitting 53 and a stainless steel FNPT fitting 54. An annular gap is formed between the inner surface of the outer jacket and the outer surface of the vapor sample conduit tubing member to provide an insulating thermal barrier preventing heat transfer between the two surfaces. The annular gap may incorporate periodic internal spacing standoffs or a continuous insulating foam/layer encasing the outer surface of the tubing member 51 if required for regulatory purposes.

A vacuum pump-out nipple 55 is provided near one end of the jacket 52 to permit evacuation of the jacket. The vacuum jacket must possess sufficient hoop strength to withstand collapse/imploding upon creation of an internal vacuum and permit bending without creasing or pinching. A substantial length of this assembly is encased with an outer casing 56 formed from a bendable/flexible material such as a rugged, reinforced elastomeric pipe or non-rusting, spiral metal jacketing that allows an installer in the field to bend the tubing 24 without damaging the tube at least during the installation thereof.

Figure 7:
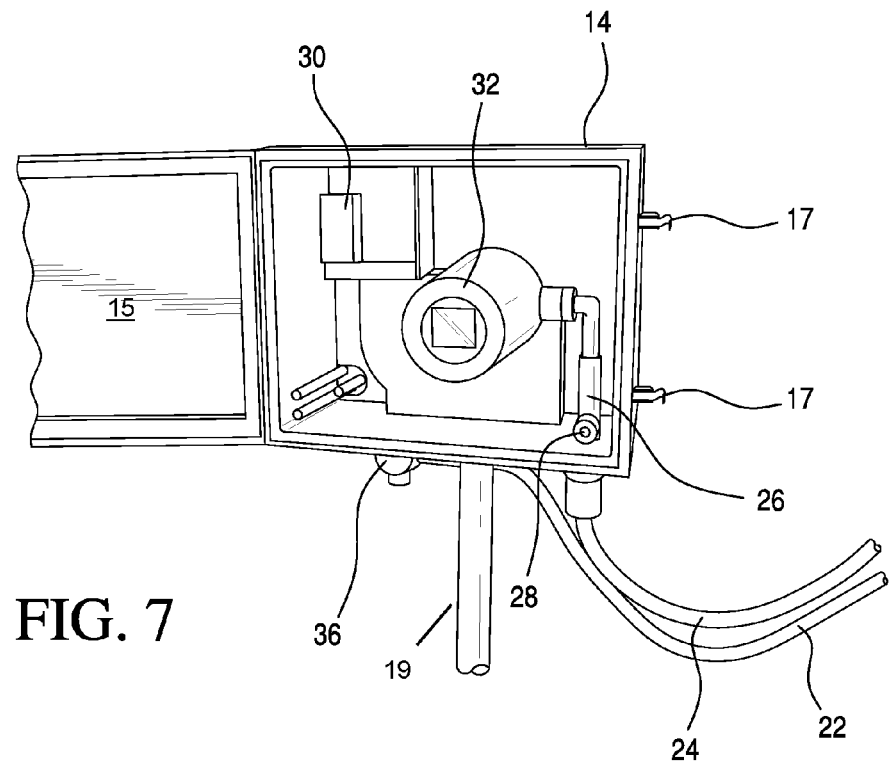
FIG. 7 is a front view of the interior of the analyzer cabinet according to FIG. 1.

The vacuum for the vacuum jacketed tubing is created by attachment of a vacuum pump (not illustrated) to the nipple 55 which is associated with a vacuum port 26 (see FIG. 7) to establish a quantitatively sufficient thermally insulating vacuum. The vacuum port 26 includes a vacuum indicator 28 to visually indicate the presence of an adequate vacuum. In one form, the indicator may be a simple mechanical spring biased detentable red button which will move to and/or protrude from the front of the housing in the event of a vacuum failure. In this manner a field worker is able to visually assess the need to re-evacuate the tubing upon minimal inspection of the system. (A low power LED indicator and detecting circuitry may be substituted for the simpler mechanical indicator but with the appreciation that such a unit requires slightly more complex wiring and slightly greater system energy consumption).

Proximate to the above-mentioned carrier gas input port 34 associated with the analyzer component 14, preferably positioned on a side thereof to avoid interference with access to the interior and pivoting of door 15, is an all-weather carrier gas tank retaining bracket 38 for releasably mounting a conventional carrier gas (e.g., helium) containing tank and valve regulator to the exterior of analyzer 14. The illustrated tank mounted valve regulator 39 is a typical manually operated type and feeds the helium carrier gas to the enclosed gas chromatograph 32 as controlled by the flow controller 30. When desired, the wireless communication facility 42 may also be incorporated with the analyzer component 14 to provide control and reporting communication with a remote base so long as the facility 42 is heat resistant to the operating temperature of the cabinet particularly when heated (See FIG. 1).

Figure 3:
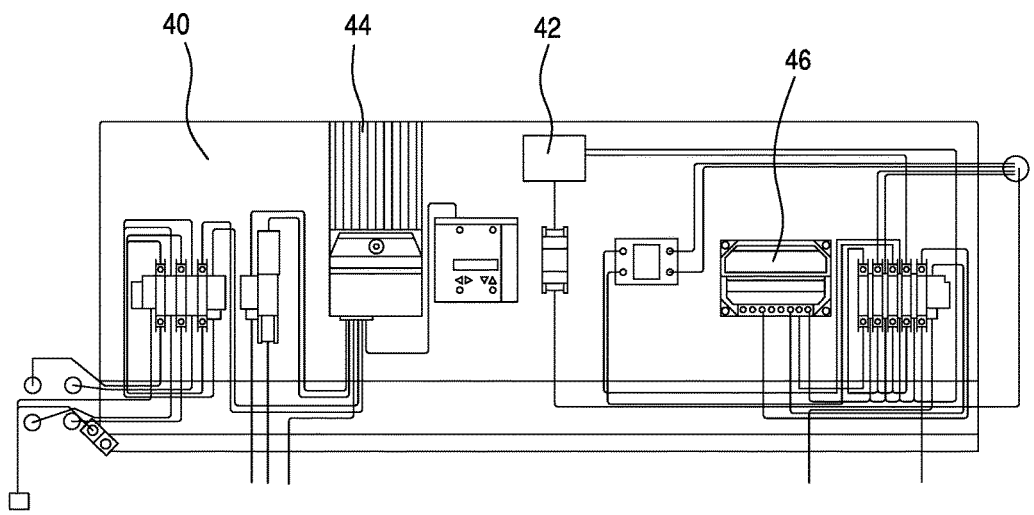
FIG. 3 is a wiring schematic of the control system circuitry of the embodiment in FIG. 2.

Turning now to the third component, it is a power generation and storage module including an inter-connected array of deep-cycling battery-type energy storage cells, a power control center, an exteriorly mounted and electrically connected solar power collecting photovoltaic cell array in the form of a panel which preferably is disposed to provide shading to the battery/control enclosure and, unless incorporated into the analyzer cabinet 14 (see FIG. 1), a wireless, radio modem 42 for transmitting analytical data output from the analyzer 32 (see FIG. 3).

Figure 4:
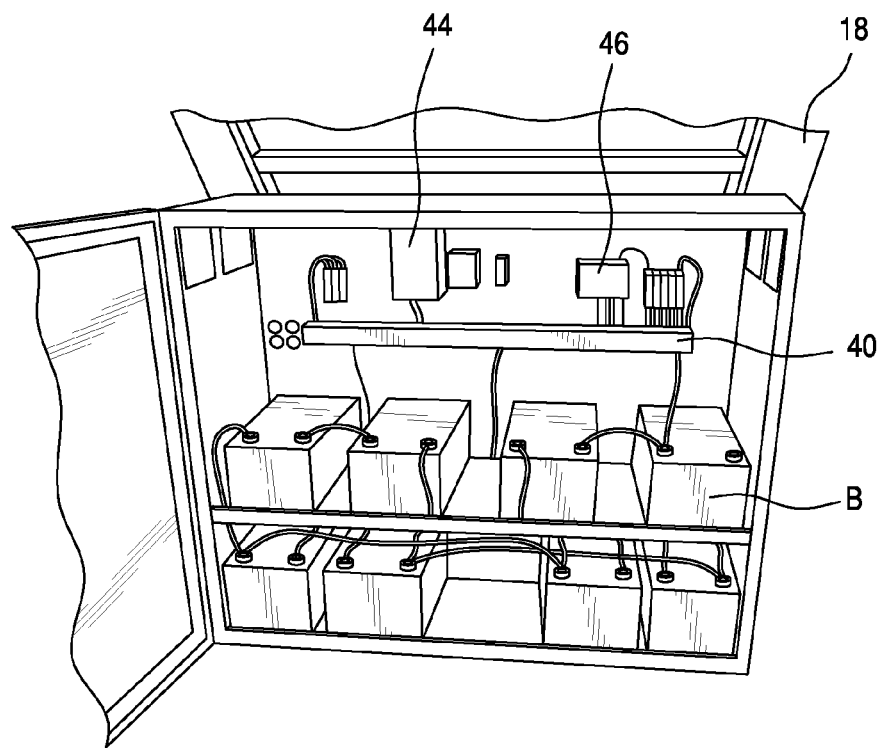
FIG. 4 is a schematic representation of a storage battery enclosure with an array of interconnected storage cells according to an embodiment of the invention.
Figure 5:
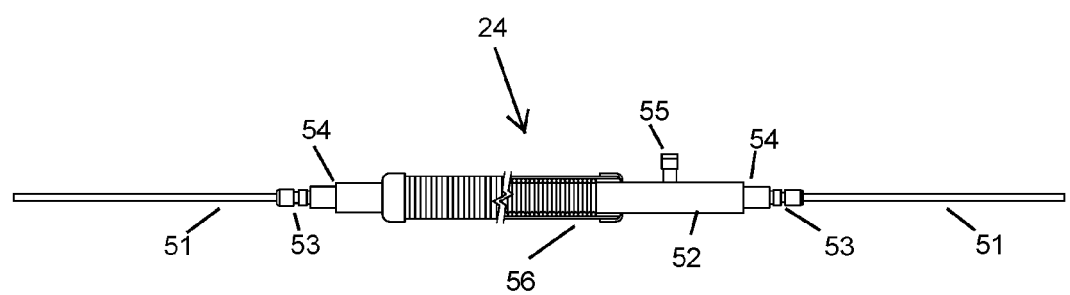
FIG. 5 is a schematic representation of bendable vacuum jacketed tubing assembly according to the invention.
Figure 6:
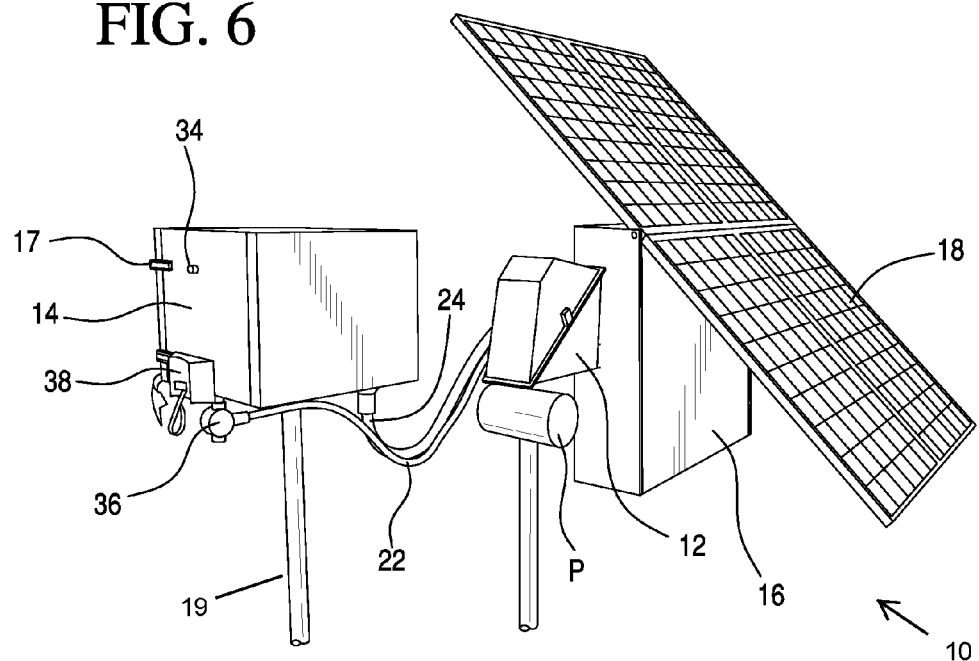
FIG. 6 is a side perspective view of the embodiment of FIG. 1 of the invention.

The third component comprises solar-panel-mounting, power generation/storage, power control, and communication containing module 16. The enclosure/module 16, schematically represented in FIGS. 2-4, features a weatherproof enclosure 48 capable of housing power control circuitry 40 of the type illustrated in FIGS. 2 and 3 communications facilities such as a wireless modem 42 for transmitting to and receiving digital data from a distant central control center, an inter-connected array of deep-cycling, low self-discharge storage batteries, e.g., 12 v-250 Ah Valve Regulated Lead Acid (VRLA) sealed batteries storage cells B (in this case eight) connected in series and powered by an exteriorly mounted photovoltaic panel 18. The module 16 is connected by power transmitting conduit 19 to the analyzer and preferably takes the form of heat tracing.

The enclosure 48 is a sturdy vented cabinet formed, preferably of a powder-coated, welded steel frame, panels, and hinge mounted front panel that allows for easy interior access. The enclosure provides internal space for placement of a shelved array of energy storage batteries to provide sufficient gaps for adequate airflow and ample wall space for secure mounting of control and communications equipment. The enclosure also provides a pivotal mounting for the solar panel 18 that permits angular adjustability and prevents the panel base from contacting the ground and fittings for cables and wiring feedthroughs. Preferably, the panel 18 is positioned to maximize solar energy collection while providing shade to the enclosure to avoid unnecessary heat build-up. The illustrated cabinet is a. Preferably that unit also includes the required batteries and MorningStar brand charge and load controllers.

Figure 2:
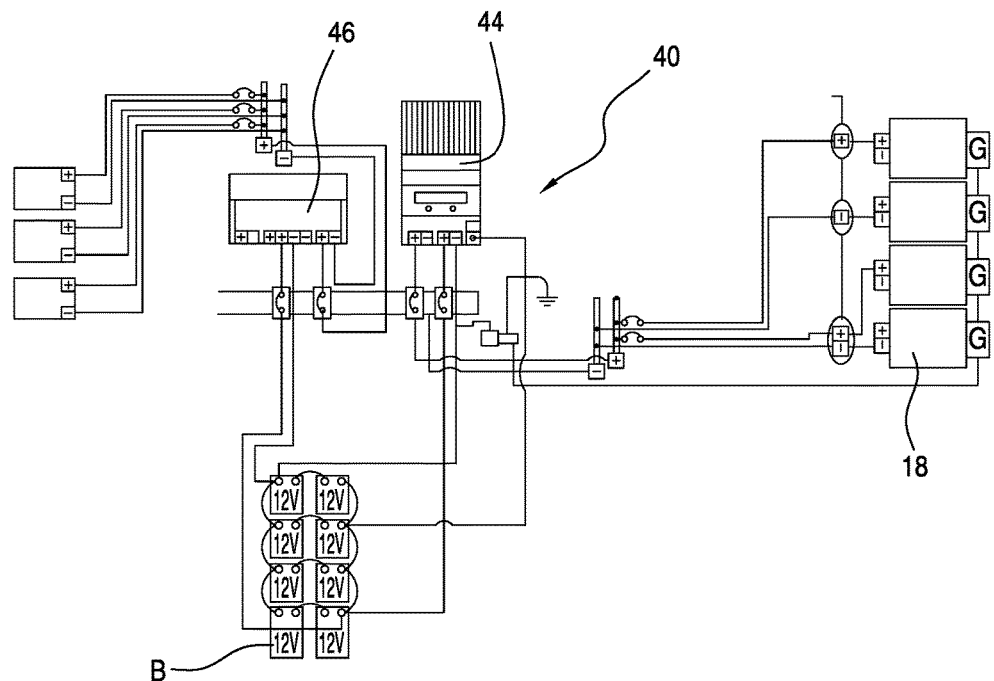
FIG. 2 is a schematic for a battery storage and control system for a solar powered sample conditioning and analyzing system according to the invention.

An exemplary arrangement of the power control unit uses a DPW Power Fab Battery Box model BB10-8D+4 enclosing circuitry 40 is illustrated in FIGS. 2 and 3. In that schematic, a solar panel 18 is a 1080 watt array connected to a charge controller 44 such as a Morningstar model TS-MPPT-60 available from Morningstar Corporation of Newton, Pa., US to input to the battery array B arranged both in series and parallel as illustrated in FIG. 2. The Morningstar controller, rated for photovoltaic current and load at 60 A, provides for four Stage charge control, includes data logging functionality, adjustable set points and temperature compensation.

A load controller 46 outputs the stored electrical power at 24V at select amperages adequate to operate the target instruments and equipment located in the enclosure 16 as well as the flow controller and analyzer of the analyzer cabinet 12 (and the communicating equipment if not located in the power enclosure 16), and the heated regulator of the probe takeoff unit 12. The illustrated embodiment incorporates a Morningstar Pro Star-30 controller includes automatic recovery functionality and internal electronic protections against short circuits, overload, reverse polarity, current reversal when dark, high voltage and temperature disconnect, and lightning and transient surge protection.

In view of the foregoing description, alternative embodiments should be apparent. For example, a multi-stage temperature and pressure regulator may be located directly atop the takeoff probe with an associated low power heat block to maintain consistent inlet/outlet temperatures and pressures and thereby avoid flashing resulting from an imbalance thereof. In another embodiment, conditions permitting and where separation of the power supply component is not expected to be moved or separated from the take-off and analyzer components when a conventional power supply is available, the second, analyzer and third power supply components may be secured within a common cabinet. A further alternative construction to the above-mentioned electrical conduit connection 22 and VJT 24 between the first and second enclosures, involves integrating the wiring/tracing cable with the vacuum jacketed tubing and have appropriate connectors hermetically sealed and projecting from the ends of the outer tube of the vacuum jacketing.

Although the described embodiment of the invention and the variations thereof has been disclosed in the forgoing specification, it is understood by those skilled in the art that many modifications and embodiments of the invention will come to mind to which the invention pertains, particularly having the benefit of the teaching presented in the foregoing description and associated drawing. It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description of the invention.

We claim:

1. A system for extracting and analyzing fluid sample from a pipeline, the system comprising:
    a pipeline sample take-off probe;
    a take-off conduit connecting said takeoff probe to a sample conditioner to generate a vaporized fluid sample, said sample conditioner including an electrically powered heater element, a pressure regulator, flow controller, and a conditioned vapor sample output;
    a vacuum jacketed insulated tubing defined by an outer tubular casing with an inner surface and an inner tubular vaporized fluid sample conduit member an inner and outer surface, said inner tubular vaporized sample fluid conduit member with a first and a second end where the first end is attached to said conditioned vapored-fluid sample output of said sample conditioner, said inner tubular vaporized fluid sample conduit member being substantially coextensive with and coaxially disposed within said outer tubular casing and spaced therefrom so as maintain space between it and said inner surface of said outer tubular casing to form a thermal insulating annulus between said outer casing inner surface and said inner tubular vaporized fluid sample conduit member outer surface, and said inner tubular vaporized fluid sample conduit member defining a wall having a thickness sufficient to possess a pressure rating in excess of 500 psig (35 bar) and said inner tubular vaporized fluid sample conduit member having an inner diameter dimensioned to maintain sufficient pressure and flow rate to avoid flashing of said vaporized fluid sample during transit threrethrough, and
    an electrically powered analyzer unit including a low power vapor analyzer for qualitative and quantitative detection of at least one analyte in said conditioned vaporized fluid sample, said analyzer unit having an inlet in vapor communication with said second end of the tubular vaporized fluid sample conduit member for receiving said conditioned vapor sample, an input for a carrier gas, said electrically powered analyzer detecting the at least one analyte of the vaporized fluid sample and generating at least one signal corresponding to the obtained result;
    a low power electrical control unit including a power control center electrically connected to the conditioner and analyzer unit; and
    a photovoltaic panel with an electrical power storage array connected to the low power control unit for distribution to electrically-operated control unit.

2. The system of claim 1, wherein the electrically powered analyzer is a field-type process gas chromatograph.

3. The system of claim 1, wherein the photovoltaic panel is configured to operate at no greater than 24 volts.

4. The system of claim 1, wherein the electrically powered analyzer and the low power electrical control unit are contained in a common housing which is remotely spaced at least 3 meters (10 feet) but no more than 15 meters (50 feet) from the sample conditioner.

5. The system of claim 4 where the housing is explosion-proof and further comprising an electrically powered wireless communications module unit for transmitting the obtained result to a remote receiver where said electrically powered wireless communications module is connected to said low power electrical control unit and powered thereby.

6. The system of claim 1 where the vacuum jacketed tubing incorporates heat tracing electrical conduit for providing power to the sample conditioner, the analyzer, and low power electrical control unit which are contained in discrete separate weatherproof housings.

7. The system of claim 1 where at least one of the housings is an explosion proof cabinet.

8. The system of claim 1 where the inner tubular vaporized sample fluid conduit is stainless steel with a ¼ inch outer diameter and a wall thickness of 0.065 inches thickness with stainless steel fittings on both first and second ends to provide for reduction/enlargement to avoid flashing of the sample.

9. The system of claim 1 where the inner tubular vaporized sample fluid conduit is stainless steel with a ¹⁄₁₆-¼ inch outer diameter and a wall thickness of 0.02-0.065 inch with stainless steel fittings on both first and second ends to provide for reduction/enlargement to avoid flashing of the fluid sample, and an outer jacket that allows for non-destructive bending thereof.

10. A solar-powered system for analyzing at least one analyte in a fluid sample, the system comprising:
    a first enclosure including a heated fluid sample take-off input, a heated pressure regulator, a flow conditioner, and a conditioned sample output, wherein the first enclosure is in operable communication with a sample source and generates a conditioned vaporized sample from the fluid;
    a second enclosure operably connected to the first enclosure, said second enclosure including a conditioned sample input and an analyzing device providing a signal output representative of the vaporized sample composition;
    means for communicating said conditioned vaporized sample between said first and second enclosure in a manner to maintain thermal and flow rate stasis of the vaporized sample during transit, and
    a third enclosure including a power control center and a photovoltaic panel, said third enclosure for providing operating power to the first and second enclosures and receiving said signal from the analyzing device.

11. The system of claim 10 wherein the fluid sample is selected from the group consisting of natural gas, liquefied natural gas, compressed natural gas, cryogenic fluid, and biogas.

12. The system of claim 11 further comprising an electronic communications module includes a wireless modem for transmitting data from the analyzer and receiving instructions from a remote source.

13. The system of claim 10, where the vacuum jacketed insulated tubing incorporates a sample conduit of stainless steel tubing with a 1/16-1/4 inch (3-8 mm) outer diameter and a wall thickness of 0.02-0.065 inch (0.05-0.15 mm) and, stainless steel fittings on first and second ends of said sample conduit to provide for reduction/enlargement that avoids flashing of the sample, and an outer jacket that allows for non-destructive bending thereof.

14. The system of claim 10, wherein the system is configured to maintain a sample temperature during transit between the first enclosure and that of the second enclosure above a dew point dropout temperature.

15. A method for remotely analyzing samples using the system of claim 1, wherein during transit between the sample conditioner enclosure and the analyzer, of the sample is maintained above a dew point dropout temperature.

16. A method for remotely analyzing samples using the system of claim 10, wherein during transit between the first enclosure and the second enclosure, the sample is maintained above a dew point dropout temperature.

* * * * *